(12) United States Patent
Chiang et al.

(10) Patent No.: US 6,583,181 B1
(45) Date of Patent: Jun. 24, 2003

(54) ANTIMICROBIAL QUATERNARY AMMONIUM COMPOSITIONS WITH REDUCED OCULAR IRRITATION

(75) Inventors: Michael Yao-Chi Chiang, Flemington, NJ (US); Larry Kent Hall, Northampton, PA (US)

(73) Assignee: Lonza Inc., Fair Lawn, NJ (US)

( * ) Notice: Subject to any disclaimer, the term of this patent is extended or adjusted under 35 U.S.C. 154(b) by 8 days.

(21) Appl. No.: 09/721,523

(22) Filed: Nov. 22, 2000

(51) Int. Cl.⁷ .............................................. A61K 31/14
(52) U.S. Cl. ........................ 514/642; 514/563; 514/912
(58) Field of Search ................................ 514/563, 642, 514/912

(56) References Cited

U.S. PATENT DOCUMENTS

| | | | |
|---|---|---|---|
| 5,547,990 A | 8/1996 | Hall et al. | 514/563 |
| 6,080,789 A | 6/2000 | Lutz | 514/642 |
| 6,297,285 B1 | 10/2001 | Lutz | 514/642 |

OTHER PUBLICATIONS

"Evaluation of the Toxicity of Benzalkonium Chloride on the Ocular Surface", Caroline Debbasch, et al., *J.Toxicol. Cut. & Ocular Toxicol.*, 19(2&3), pp. 105–115 (2000).
"Effect of Alkaline Builders and Surfacants on the Bactericidal Activity Of Didecyldimethylmmonium Chloride", *J. Antibact. Antifung. Agents*, vol. 20, No. 12, pp. 617–622 (1992).

Primary Examiner—Zohreh Fay
(74) Attorney, Agent, or Firm—Darby & Darby

(57) ABSTRACT

The present inventors have discovered that electrolytes, such as the tetrasodium salt of ethylenediaminetetraacetic acid (EDTA), reduce the ocular irritation and increase the disinfecting and sanitizing efficacy of compositions containing quaternary ammonium compounds and/or amines. As a result, concentrated solutions containing quaternary ammonium compounds and/or amines of the present invention have low, if any, ocular irritation. Furthermore, use dilutions of the concentrated solutions of the present invention include ingredients which are approved by the U.S. EPA for use on indirect food contact surfaces, unlike disinfecting and sanitizing compositions containing imidazoline compounds. Additionally, the use dilutions exhibit superior efficacy against gram negative and positive bacteria compared to similar compositions which do not contain the electrolyte and remain effective in hard water. The present invention is a concentrate, such as a sanitizing and disinfecting concentrate, comprising from about 0.5 to about 4.0% by weight of a quaternary ammonium compound, an amine, or a combination thereof and from about 2.0 to about 15.0% by weight of electrolyte, based upon 100% total weight of concentrate. The concentrate is generally substantially free of imidazoline compounds. Another embodiment is an ophthalmic solution comprising a quaternary ammonium compound, an amine, or a combination thereof, at least one electrolyte, and, optionally, a biologically active agent.

8 Claims, No Drawings

ANTIMICROBIAL QUATERNARY AMMONIUM COMPOSITIONS WITH REDUCED OCULAR IRRITATION

FIELD OF THE INVENTION

This invention relates to sanitizing and disinfecting compositions and ophthalmic solutions containing a quaternary ammonium compound, an amine, or a combination thereof and an electrolyte, which cause little, if any, ocular irritation.

BACKGROUND OF THE INVENTION

Sanitizers and disinfectants are formulations intended to reduce or destroy pathogenic bacteria, fungi and viruses. Quaternary ammonium compounds serve as the active antimicrobial agent in a wide variety of these formulations which are currently used in the household, industrial and institutional markets. They are typically effective at low concentrations and provide a broad spectrum of bactericidal activity, against both gram positive and gram negative bacteria. In addition to the antimicrobial agent, the formulations usually contain co-surfactants to assist in solubilizing soil particulates. As labor costs have been increasing substantially, there has been a trend toward one-step disinfectant cleaners, i.e., formulations which both clean and disinfect or sanitize in one application. This concept has also become attractive for the household market as well, where reducing cleaning time is desirable.

Unfortunately, many quaternary ammonium compounds, such as dialkyl quaternary ammonium chlorides, being cationic surfactants, are irritating to ocular tissue.

U.S. Pat. No. 5,547,990 discloses the use of certain substituted imidazoline based amphoterics to reduce the ocular irritation caused by quaternary ammonium compounds. These amphoterics, however, have not been approved by the U.S. Environmental Protection Agency (EPA) for use on indirect food contact surfaces, such as cutting boards, utensils, containers, dishes, and wash basins.

With increased concerns over pathogens in the household environment, the need for safe disinfectants and sanitizers has increased. Therefore, there is a continuing need for safe and mild household disinfectants and sanitizers which do not cause ocular irritation and are suitable for indirect food contact surfaces.

It has recently been discovered that benzalkonium chloride, a widely used preservative in ophthalmic solutions, may induce irreversible cytotoxic damage. See C. Debbasch et al., *J. Toxicol.-Cut. & Ocular Toxicol.*, 19(2&3), 105–115 (2000). Therefore, there is a continuing need for preservatives for ophthalmic solutions which do not cause cytotoxic damage or ocular irritation.

SUMMARY OF THE INVENTION

The present inventors have discovered that electrolytes, such as the sodium salt of ethylenediaminetetraacetic acid (EDTA), reduce the ocular irritation and increase the disinfecting and sanitizing efficacy of compositions containing quaternary ammonium compounds or amines. As a result, concentrated solutions containing quaternary ammonium compounds and/or amines of the present invention have low, if any, ocular irritation. Furthermore, use dilutions of the concentrated solutions of the present invention include ingredients which are approved by the U.S. EPA for use on indirect food contact surfaces, unlike disinfecting and sanitizing compositions containing imidazoline compounds. Additionally, the use dilutions exhibit superior efficacy against gram negative and positive bacteria compared to similar compositions which do not contain the electrolyte and remain effective in hard water.

The present invention is a concentrate, such as a sanitizing and disinfecting concentrate, comprising from about 0.5 to about 4.0% by weight of a quaternary ammonium compound, an amine, or a combination thereof and from about 2.0 to about 15.0% by weight of electrolyte, based upon 100% total weight of concentrate. The concentrate is generally substantially free of imidazoline compounds. Use dilutions of the concentrate of the present invention have superior efficacy against both gram negative and positive bacteria compared to similar compositions which do not contain the electrolyte. Furthermore, use dilutions of the concentrate remain effective in water having a hardness of at least 200, 300, 400, and even 750 ppm.

Another embodiment is an ophthalmic solution comprising a quaternary ammonium compound, an amine, or a combination thereof, at least one electrolyte, and, optionally, a biologically active agent. The ophthalmic solution generally comprises from about 0.5 to about 4.0% by weight of quaternary ammonium compound and amine and from about 1.0 to about 15.0% by weight of electrolyte, based upon 100% total weight of ophthalmic solution. The quaternary ammonium compound and amine typically act as a preservative. The electrolyte prevents the quaternary ammonium compound and amine from irritating the eye of anyone who is administered the ophthalmic solution. The electrolyte also neutralizes the toxic effects of the quaternary ammonium compound and amine. The solution is generally substantially free of imidazoline compounds.

DETAILED DESCRIPTION OF THE INVENTION

The present inventors have discovered that electrolytes at certain concentrations reduce, if not eliminate, ocular irritation due to quaternary ammonium compounds and amines.

Concentrates

One embodiment of the present invention is a concentrate comprising from about 0.5 to about 4.0% by weight of a quaternary ammonium compound, an amine, or a combination thereof and from about 2.0 to about 15.0% by weight of electrolyte, based upon 100% total weight of concentrate. The concentrate preferably comprises from about 1.0 to about 3.0% and more preferably from about 1.0 to about 2.0% by weight of quaternary ammonium compound, amine, or a combination thereof. The concentrate also preferably comprises from about 2.0 to about 10.0% and more preferably from about 4.0 to about 8.0% by weight of electrolyte.

The quaternary ammonium compound or amine may be any antimicrobial, antifungal, or antibacterial quaternary ammonium compound or amine. Preferably, the quaternary ammonium compound and/or amine effectively disinfects and/or sanitizes substrates. Suitable quaternary ammonium compounds include, but are not limited to, those having the formula:

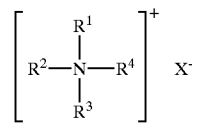

where $R^1$ is a linear or branched $C_1$–$C_4$ alkyl or linear or branched $C_1$–$C_4$ alkoxy; $R^2$ is a linear or branched $C_1$–$C_{18}$ alkyl or linear or branched $C_1$–$C_{18}$ alkoxy; $R^3$ is a linear or branched $C_6$–$C_{18}$ alkyl or is —$R^5$—O—$R^6$—O($C_6H_5$)$R^7$, wherein $R^5$ and $R^6$ are independently linear or branched $C_1$–$C_8$ alkyl and $R^7$ is linear or branched $C_1$–$C_{12}$ alkyl; $R^4$ is a linear or branched $C_6$–$C_{18}$ alkyl, benzyl, or ($C_1$–$C_{18}$ alkyl)benzyl; and X is an anion. According to a preferred embodiment, $R^3$ and $R^4$ are independently $C_8$–$C_{18}$ alkyl and more preferably $C_8$–$C_{12}$ alkyl. According to another preferred embodiment, $R^3$ is a $C_{12}$–$C_{18}$ alkyl and $R^4$ is benzyl. Suitable anions include, but are not limited to, halogens, such as chloride, bromide, iodide, and fluoride, and carbonate.

Suitable quaternary ammonium compounds include, but are not limited to, alkyldimethylbenzyl ammonium chlorides, dialkylmethylbenzyl ammonium chlorides, dialkyldimethylammonium chlorides, alkyl dimethyl ethylbenzyl quaternary ammonium chlorides, benzethonium chloride (available as Hyamine® 1622 from Lonza Inc. of Fair Lawn, N.J.), and any combination of any of the foregoing.

Non-limiting examples of alkyldimethylbenzyl ammonium chlorides include alkyl ($C_{14}$ 50%; $C_{12}$ 40%, $C_{16}$ 10%) dimethylbenzyl ammonium chloride (available as Barquat® MB-50 and MB-80 from Lonza Inc.), alkyl ($C_{14}$ 60%; $C_{16}$ 30%; $C_{12}$ 5%. $C_{18}$ 5%) dimethylbenzyl ammonium chloride (available as Barquat® 4280Z from Lonza, Inc.), ($C_{12}$–$C_{18}$ alkyl) dimethylbenzyl ammonium chloride, and any combination of any of the foregoing.

Non-limiting examples of dialkyldimethyl ammonium chlorides include dioctyldimethylammonium chloride (available as Bardac® LF and LF-80 from Lonza, Inc.), octyldecyldimethylammonium chloride (available as a mixture of octyldecyldimethylammonium chloride, dioctyldimethylammonium chloride, and didecyldimethyl ammonium chloride as Bardac® 2050 and 2080 from Lonza, Inc.), didecyldimethylammonium chloride (available as Bardac® 2250 and 2280 from Lonza, Inc.), decylisononyldimethylammonium chloride (available as Bardac® 21 from Lonza, Inc.), diisodecyldimethylammonium chloride (available as BTC 99 from Stepan Co. of Northfield, Ill.), and any combination of any of the foregoing.

Suitable amines include, but are not limited to, tertiary amines, such as ($C_8$–$C_{14}$) alkyl amines. The term "($C_8$–$C_{14}$) alkyl amine" encompasses all amines which contain a ($C_1$–$C_{14}$) alkyl group. A preferred ($C_8$–$C_{14}$) alkyl amine is N,N-bis(3-aminopropyl)dodecylamine, available as Lonzabac® 12.30 and 12.100 from Lonza, Inc.

Any electrolyte known in the art may be included in the concentrate. Special mention is made of salts of ethylenediaminetetraacetic acid (EDTA), including sodium EDTA (such as mono-, di-, tri-, and tetra-sodium salts of EDTA); carbonates, such as sodium carbonate and sodium bicarbonate; sodium glycolate; sodium chloride; calcium chloride; and any combination of any of the foregoing. Other suitable salts of EDTA include, but are not limited to, ammonium salts, potassium salts, and carbonates of EDTA. More preferably, the electrolyte is sodium EDTA.

The electrolyte reduces the ocular irritation and increases the disinfecting and sanitizing efficacy of the quaternary ammonium compound and/or amine. Without being bound by any theory, the inventors believe that the electrolyte stimulates the eye membrane to produce a small amount of tears which reduces the irritation effect of the quaternary ammonium compound and/or amine.

The weight ratio of quaternary ammonium compound and amine to electrolyte in the concentrate broadly ranges from about 10:1 to about 1:10 and preferably ranges from about 2:1 to about 1:4.

The concentrate can also include additives, such as chelators, builder salts, dyes, fragrances, and nonionic surfactants, such as those commonly used in the art of cleaning and disinfecting solutions.

Non-limiting examples of chelators include citric acid, nitriloacetic acid, phosphoric acids, zeolites, and any combination of any of the foregoing. The concentrate generally contains from about 0.1 to about 10% and preferably from about 1.0 to about 7.0% by weight of chelator, based upon 100% total weight of concentrate.

Non-limiting examples of builder salts include sodium metasilicate, sodium tripolyphosphate, sodium nitrilotriacetate, sodium carbonate, sodium silicate, citric acid salts, zeolites, and any combination of any of the foregoing. The concentrate generally contains from about 0.1 to about 15% and preferably from about 0.5 to about 2.0% by weight of builder salt, based upon 100% total weight of concentrate.

Suitable nonionic surfactants include, but are not limited to, amine oxides, nonylphenol ethoxylates, linear alcohol ethoxylates, secondary alcohol ethoxylates, ethoxylated propoxylated (EOPO) block polymers, and any combination of any of the foregoing. The concentrate generally comprises from about 0.1 to about 25% and preferably from about 0.5 to about 10% by weight of nonionic surfactant, based upon 100% total weight of concentrate.

The pH of the concentrate preferably ranges from about 6.0 to about 8.5 and more preferably from about 6.5 to about 7.5.

The sanitizing concentrate is generally substantially free of imidazoline compounds, such as those described in U.S. Pat. No. 5,547,990, which is hereby incorporated by reference. Preferably, the concentrate contains less than 1% and, more preferably, less than 0.1% by weight of imidazoline compounds, based upon 100% total weight of concentrate.

Typically, the concentrate is diluted with a solvent, such as water and propylene glycol, prior to use. The use dilution (and concentrate) exhibit broad bactericidal activity against both gram positive and gram negative bacteria, including, but not limited to, *E. coli* and *S. aureus*. The use dilution broadly contains a sanitizing, disinfecting, antimicrobial, antifungal, and/or antibacterial effective amount of the quaternary ammonium compound and/or amine. For example, the concentrate may be diluted to 1:128 of its original concentration. At such a dilution, the use dilution broadly contains 1.92 to 2.56% by weight of the quaternary ammonium compound and/or amine, based upon 100% total weight of use dilution. Typically, the use dilution contains from about 1 to about 400 ppm of the quaternary ammonium compound and/or amine. According to a preferred embodiment, the use dilution contains 150 to 200 ppm of the quaternary ammonium compound and/or amine.

Also, the use dilution preferably contains an effective amount of electrolyte to prevent ocular irritation due to the quaternary ammonium compound and/or amine.

In one embodiment, the use dilution contains an aqueous solvent comprising hard water of at least 200, 300, 400, 500, or 750 ppm of water hardness. As discussed above, the concentrate and use dilution of the present invention remain effective against microorganisms, such as pathogenic bacteria, in hard water.

The use dilution may be applied to a substrate in order to disinfect and/or sanitize the substrate. The use dilution may be applied by any method known in the art including, but not limited to, brushing, spraying, soaking, and the like. For example, the use dilution may be absorbed or incorporated into wipes which are then rubbed against a substrate. The use dilution may also be used in clean-in-place applications, i.e., by recirculating the use dilution in pipes, kettles, tanks, and the like to clean, disinfect, and/or sanitize the same.

Substrates which may be sanitized and disinfected with the use dilution include, but are not limited to, those located in dairies, homes, swimming pools, canneries, food processing plants, restaurants, hospitals, institutions, and industry, including secondary oil recovery. For example, the use dilution can be used to sanitize diary plant equipment, milking machines, milk pails, tank trucks, and the like. The use dilution can also be used to sanitize floors, walls, furniture, mirrors, toilet fixtures, and wood surfaces, such as fence rails, porch rails, decks, roofing, siding, window frames, and door frames. The use dilutions are particularly well suited for application on indirect food contact surfaces, such as cutting boards, utensils, containers, dishes, wash basins, and countertops.

The use dilution may also be applied to the skin, such as the hands or face, in order to disinfect and sanitize them. For instance, the use dilution or concentrate of the present invention may be incorporated into a hand dip or hand soap, such as that used by workers in the meat and poultry industry and the medical fields. Alternatively, the use dilution may be absorbed or incorporated into personal care items, such as facial and hand wipes.

The use dilution or concentrate may also be incorporated into sanitizing laundry rinses.

The concentrate and use dilution may be prepared by any method known in the art. For example, they may be prepared by mixing the quaternary ammonium compound and/or amine, electrolyte, solvent, and other additives. The use dilution may also be prepared by adding a solvent, such as water, to the concentrate.

Ophthalmic Solution

Another embodiment of the invention is an ophthalmic solution comprising a quaternary ammonium compound, an amine, or a combination thereof, an electrolyte and, optionally, a biologically active agent. The ophthalmic solution typically contains an antimicrobial, antibacterial, and/or antifungal effective amount of quaternary ammonium compound and/or amine. According to one preferred embodiment, the quaternary ammonium compound and/or amine acts as a preservative in the ophthalmic solution. The ophthalmic solution generally contains an effective amount of the electrolyte to prevent ocular irritation due to the quaternary ammonium compound and amine and to neutralize the toxic effects of the quaternary ammonium compound or amine.

The aforementioned quaternary ammonium compounds and electrolytes may also be included in the ophthalmic solution. More preferred quaternary ammonium compounds include, but are not limited to, benzalkonium chlorides, such as alkyl benzyl dimethyl ammonium chlorides, and benzethonium chloride.

The ophthalmic solution broadly contains from about 0.05 to about 2.0%, preferably from about 0.1 to about 1.0%, and more preferably from about 0.2 to about 0.8% by weight of quaternary ammonium compound, amine, or a combination thereof, based upon 100% total weight of ophthalmic solution. The ophthalmic solution broadly contains from about 1.0 to about 15.0%, preferably from about 3.0 to about 8.0%, and more preferably from about 4.0 to about 6.0% by weight of electrolyte, based upon 100% total weight of ophthalmic solution.

The weight ratio of quaternary ammonium compound and amine to electrolyte in the solution broadly ranges from about 10:1 to about 1:10 and preferably ranges from about 2:1 to about 1:4.

Preferred biologically active agents include, but are not limited to, those which may be administered by the ocular route. A non-limiting example of such an agent is an antiglaucoma agent, such as pilcocarpine, timodol maleate, carbachol, isoflurophate, epinephrine, dipvefrin, and demecarium bromide.

The ophthalmic solution typically includes an amount of the biologically active agent effective for its intended use. For example, an ophthalmic solution containing antiglaucoma agent can contain an antiglaucoma effective amount of the agent.

The ophthalmic solution may include other additives as known in the art.

The ophthalmic solution is generally substantially free of imidazoline compounds. Preferably, the ophthalmic solution contains less than 0.1% and, more preferably, less than 0.01% by weight of imidazoline compounds, based upon 100% total weight of ophthalmic solution.

The ophthalmic solution is generally administered ocularly in the form of droplets or as an eye wash. For instance, an ophthalmic solution of the present invention containing an antiglaucoma agent may be ocularly administered to an animal, such as a human, in need thereof to treat glaucoma.

The ophthalmic solution may be prepared by any method known in the art. For example, the solution may be prepared by mixing the quaternary ammonium compound and/or amine, electrolyte, biologically active agent, solvent, and other additives.

The following examples are illustrative of the present invention, however, it will be understood that the invention is not limited to the specific details set forth in the examples. All percentages are by weight unless otherwise indicated.

EXAMPLE 1

The formulation in Table 1 below was prepared by mixing the appropriate ingredients. The ocular irritation of each formulation was determined by the Draize rabbit eye test, which is an acute eye irritation evaluation method currently accepted by the U.S. Environmental Protection Agency (EPA). The Draize rabbit eye test is described in *Principles and Procedures for Evaluating the Toxicity of Household Products*, National Academy of Science Publication 1138 (1977), which is hereby incorporated by reference. Briefly, in the Draize rabbit eye test, three or six rabbits are used. A test formulation is administered to one eye of each rabbit. The other eye is used as a control. The eyes are compared at various timepoints for cornea opacity, damage to the iris, and damage to the conjunctiva. Higher draize scores indicate increased ocular irritation. A draize score of zero indicates no ocular irritation. The results are shown in Table 1.

COMPARATIVE EXAMPLE 2

The formulation described in Table 1 was prepared and tested as described in Example 1. The results are shown in Table 1.

TABLE 1

| | | Example 1 | Comparative Example 2 |
|---|---|---|---|
| Ingredients (% by weight) | NaOH (pellet) | 0.33 | — |
| | EDTA (acid) | 0.90 | — |
| | FMB ® 1210-8[1] | 1.50 | 1.50 |
| | Deionized Water | q.s. | q.s. |

TABLE 1-continued

| Characteristics | | Example 1 | Comparative Example 2 |
|---|---|---|---|
| Characteristics | pH | 7.1 | 6.9 |
| | % of Active Quaternary Ammonium Compound | 1.2 | 1.2 |
| Draize score | Day 1 | 26.3 | 41.7 |
| | Day 2 | 23.2 | 36.5 |
| | Day 3 | 20.0 | 31.8 |
| | Day 4 | 15.0 | 32.0 |
| | Day 7 | 7.7 | 30.0 |
| | Day 10 | 3.7 | — |
| | Day 14 | 0.0 | 19.7 |
| | Day 21 | — | 19.0 |

[1]FMB ® 1210-8 is a mixture of 60% by weight of Bardac ® 2280 (an 80% solution of didecyldimethyl ammonium chloride) and 40% by weight of Barquat ® MB-80 (an 80% solution of alkyl ($C_{14}$ 50%; $C_{12}$ 40%, $C_{16}$ 10%) dimethyl benzyl ammonium chloride) and is available from Lonza, Inc. of Fairlawn, N.J.

Comparative Example 2, which did not contain EDTA, had an initial Draize score of 47.1 and a Draize score of 19.0 after 21 days. In contrast, Example 1, which contained EDTA, had an initial Draize scoe of 26.3 and a Draize score of 0.0 after 14 days.

EXAMPLE 3

The formulations described in Table 2 below containing didecyl dimethyl ammonium chlorides (available as Bardac® 22 from Lonza, Inc.), alkyl ($C_{14}$ 50%, $C_{12}$ 40%, $C_{16}$ 10%) dimethyl benzyl ammonium chloride (available as Barquat® MB from Lonza, Inc.), or alkyl ($C_{14}$ 60%, $C_{16}$ 30%, $C_{12}$ 5%, $C_{18}$ 5%) dimethyl benzyl ammonium chlorides (available as Barquat® MX from Lonza, Inc.) were prepared and tested by the Draize rabbit eye test described in Example 1. The results are shown in Table 2.

EXAMPLE 4

The formulations containing alkyl ($C_{14}$ 50%; $C_{12}$ 40%, $C_{16}$ 10%) dimethyl benzyl ammonium chloride, which is available as Barquat® MB-80 from Lonza, Inc., shown in Table 3 below were prepared and tested by the Draize rabbit eye test described in Example 1. The results are shown in Table 3.

TABLE 3

| | Experiment | 1 | 2 | 3 | 4 | 5 |
|---|---|---|---|---|---|---|
| Ingredients, weight % | Barquat ® MB-80 (active) | 2.0 | 1.9 | 1.9 | 1.9 | 1.9 |
| | EDTA (acid) | — | 6.0 | 8.0 | — | — |
| | NaOH (pellets) | — | 2.4 | 3.2 | — | 3.2 |
| | NaCl, granular | — | — | — | 6.0 | — |
| | Glycolic acid, powder | — | — | — | — | 6.0 |
| | Distilled water | q.s. | q.s | q.s. | q.s. | q.s. |
| pH | | 7.0 | 7.0 | 7.2 | 7.0 | 7.0 |
| Draize score | Day 1 | 33.5 | 16.2 | 15.0 | 27.4 | 18.0 |
| | Day 2 | 29.3 | 10.7 | 13.2 | 12.7 | 17.7 |
| | Day 3 | 29.7 | 7.8 | 8.3 | 7.8 | 11.8 |
| | Day 4 | 24.5 | 4.5 | 7.8 | 6.5 | 15.0 |
| | Day 7 | 21.0 | 1.0 | 3.7 | 15.3 | 8.3 |
| | Day 10 | 14.3 | 3.3 | 3.7 | 0.0 | 0.0 |
| | Day 14 | 12.7 | 0.0 | 3.3 | — | — |
| | Day 18 | 7.6 | — | 3.7 | — | — |
| | Day 21 | 4.7 | — | 0.0 | — | — |

EXAMPLE 5

The formulations containing alkyl dimethyl benzyl ammonium chlorides (available as Barquat® MB-80 and MX-50 from Lonza, Inc.) and a mixture of alkyl dimethyl benzyl ammonium chlorides and dialkyl dimethyl ammonium chloride (available as Bardac® 205M from Lonza, Inc.) described in Table 4 below were prepared and tested by

TABLE 2

| | | Bardac ® 22 | | Barquat ® MB | | Barquat ® MB | | Barquat ® MX | |
|---|---|---|---|---|---|---|---|---|---|
| Experiment | | 1 | 2 | 1 | 2 | 1 | 2 | 1 | 2 |
| Ingredients (% by weight) | NaOH (pellet) | — | 0.4 | — | 0.4 | — | 0.48 | 0.8 | 1.6 |
| | EDTA (acid) | — | 1.0 | — | 1.0 | — | 1.2 | 2.0 | 4.0 |
| | Quaternary Ammonium Compound (active) | 1.0 | 1.0 | 1.0 | 1.0 | 1.28 | 1.28 | 2.0 | 2.1 |
| | Deionized Water | q.s. | q.s. | q.s. | q.s. | q.s. | q.s. | q.s. | q.s. |
| pH | | 7.1 | 7.5 | 7.5 | 7.4 | 7.0 | 6.9 | 7.0 | 7.0 |
| Draize score | Day 1 | 29.2 | 15.5 | 18.3 | 12.8 | 18.0 | 8.7 | 25.5 | 16.5 |
| | Day 2 | 24.5 | 11.2 | 17.8 | 7.7 | 12.7 | 3.7 | 20.5 | 9.2 |
| | Day 3 | 23.8 | 7.2 | 14.3 | 6.3 | 9.2 | 4.2 | 24.5 | 6.8 |
| | Day 4 | 22.5 | 8.5 | 10.8 | 7.0 | 7.0 | 3.0 | 20.3 | 10.8 |
| | Day 7 | 17.7 | 1.7 | 6.3 | 2.0 | 3.0 | 0.3 | 12.3 | 5.0 |
| | Day 10 | 17.3 | 1.7 | 5.7 | 0.0 | 2.0 | 0.0 | 11.7 | 1.7 |
| | Day 14 | 16.0 | 1.0 | 0.3 | — | 1.7 | — | 4.7 | 1.0 |
| | Day 18 | 9.7 | 0.0 | 0.0 | — | 1.3 | — | 0.3 | 0.0 |
| | Day 21 | 4.3 | — | — | — | 1.0 | — | 0.0 | 0.0 | the Draize rabbit eye test described in Example 1. The results are shown in Table 4.

TABLE 4

| | | Barquat® MB-80 | | Barquat® MX-50 | | Bardac® 205M[1] | |
|---|---|---|---|---|---|---|---|
| Ingredients, weight % | Quaternary Ammonium Compound (active) | 1.92 | 1.92 | 1.92 | 1.92 | 1.92 | 1.60 |
| | EDTA (acid) | 6.00 | — | 4.00 | 4.00 | — | 6.00 |
| | NaOH (pellets) | 2.40 | — | 1.62 | 1.62 | — | 2.40 |
| | NaCl, granular | — | 6.00 | — | — | 4.00 | — |
| | Distilled water | q.s. | q.s | q.s. | q.s. | q.s. | q.s. |
| Characteristics | pH | 7.0 | 6.65 | 7.1 | 7.0 | 7.3 | 7.0 |
| | Quaternary Ammonium Conc., % Actives | 2.06 | 1.94 | 2.00 | 2.0 | 2.0 | 1.71 |
| Draize score | Day 1 | 16.3 | 17.0 | 18.7 | 25.0 | 12.0 | 17.8 |
| | Day 2 | 12.8 | 11.7 | 17.5 | 14.5 | 6.7 | 17.0 |
| | Day 3 | 8.2 | 9.0 | 15.8 | 18.2 | 4.7 | 12.7 |
| | Day 4 | 3.8 | 7.2 | 13.0 | 7.7 | 3.3 | 6.5 |
| | Day 7 | 5.0 | 4.3 | 9.5 | 12.3 | 2.8 | 2.0 |
| | Day 10 | 0.7 | 4.3 | 8.0 | 1.7 | 4.3 | 0.7 |
| | Day 14 | 0.7 | 0.0 | 0.0 | 1.0 | 0.7 | 0.0 |
| | Day 18 | 0.3 | — | — | 4.3 | 0.3 | — |
| | Day 21 | 0.0 | — | — | 0.0 | 0.0 | — |

[1]Bardac® 205M is a mixture of 60% by weight of Bardac® 2050 (a 50% solution of (20% di-C₈ alkyl, 30% di-C₁₀ alkyl, 50% C₈ alkyl C₁₀ alkyl) dimethyl ammonium chloride) and 40% by weight of Barquat® MB-50 (a 50% solution of alkyl (C₁₄ 50%; C₁₂ 40%, C₁₆ 10%) dimethyl benzyl ammonium chloride)

EXAMPLE 6

A solution containing 2.4% by weight of Barquat® MB-80, 6.0% by weight of EDTA acid, 2.4% by weight of sodium hydroxide (NaOH) pellets, and a quantum sufficit of deionized water was prepared. The pH of the solution was 6.8 and the concentration of active quaternary ammonium compound in the solution was 2.0%. The solution was diluted to 1/128th of its original concentration, with water having a hardness of 500 ppm.

The effectiveness of the use dilution as a sanitizer was determined according to the Germicidal and Detergent Sanitizing Test (Food Contact Sanitizer Test) described in *Official Methods of Analysis of the AOAC*, 16$^{th}$ Edition (1995) against *Escherichia coli* and *Staphylococcus aureus*. The results are shown in Table 5 below.

TABLE 5

| Organism | Concentration of Quaternary Ammonium Compound (ppm) | Contact time | |
|---|---|---|---|
| | | 30 seconds | 60 seconds |
| *E. coli* (ATCC 11229) | 150 | 99.999% | 99.999% |
| *S. aureus* (ATCC 65) | 150 | 99.999% | 99.999% |

EXAMPLE 7

The formulations described in Table 6 below containing alkyl (C₁₄ 50%, C₁₂ 40%, C₁₆ 10%) dimethyl benzyl ammonium chloride (available as Barquat® MB from Lonza, Inc.) were prepared. The formulations were diluted to 1/128th of their original concentration with water having a hardness of 500 ppm.

The effectiveness of the use dilutions as sanitizers was determined according to the Germicidal and Detergent Sanitizing Test (Food Contact Sanitizer Test) described in *Official Methods of Analysis of the AOAC*, 16$^{th}$ Edition (1995) against *Escherichia coli*. The contact time was 30 seconds. Formulation 1 eliminated 99.9937% of the *E. coli*, which is below the U.S. EPA's standards for indirect food contact surface sanitizers as described in U.S. EPA DIS/TSS-4. Formulation 2 eliminated 99.999% of the *E. coli* and therefore exceeds the U.S. EPA's standards for indirect food contact surface sanitizers.

TABLE 6

| | | Formulation 1 | Formulation 2 |
|---|---|---|---|
| Ingredients (% by weight) | NaOH (pellet) | — | 1.6 |
| | EDTA (acid) | — | 4.0 |
| | Barquat® MB (active) | 2.0 | 2.0 |
| | Deionized Water | q.s. | q.s. |
| pH | | 7.0 | 7.1 |

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A method of preventing ocular irritation due to a solution containing a quaternary ammonium compound comprising adding an effective amount of an electrolyte to the solution to prevent ocular irritation due to the quaternary ammonium compound.

2. The method of claim 1, wherein the electrolyte is a sodium salt of ethylenediaminetetraacetic acid.

3. The method of claim 1, wherein the weight ratio of quaternary ammonium compound to electrolyte ranges from about 10:1 to about 1:10.

4. An aqueous composition consisting of:
   a) from about 0.5 to about 4.0% by weight of a quaternary ammonium chloride; and
   b) from about 4.0 to about 15.0% by weight of at least one electrolyte selected from sodium salts of ethylenediaminetetraacetic acid, sodium glycolate, sodium chloride, and mixtures thereof, based upon 100% total weight of composition, wherein the composition is free of imidazoline compounds.

5. The aqueous composition of claim 4, wherein the quaternary ammonium compound has the formula

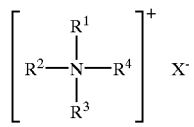

wherein
   $R^1$ is a linear or branched $C_1$–$C_4$ alkyl or linear or branched $C_1$–$C_4$ alkoxy;
   $R^2$ is a linear or branched $C_1$–$C_{18}$ alkyl or linear or branched $C_1$–$C_{18}$ alkoxy;

$R^3$ is a linear or branched $C_6$–$C_{18}$ alkyl or is —$R^5$—O—$R^6$—O($C_6H_5$)$R^7$;

$R^4$ is a linear or branched $C_6$–$C_{18}$ alkyl, benzyl, or ($C_2$–$C_{18}$ alkyl) benzyl;

$R^5$ and $R^6$ are independently linear or branched $C_1$–$C_8$ alkyl;

$R^7$ is linear or branched $C_1$–$C_{12}$ alkyl; and

X is an anion.

6. The aqueous composition of claim 5, wherein the quaternary ammonium compound is selected from the group consisting of alkyldimethylbenzyl ammonium chloride, dialkylmethylbenzyl ammonium chloride, dialkyldimethylammonium chloride, alkyldimethylethylbenzyl ammonium chloride, diisobutylphenoxyethoxyethyl chloride, and any combination of any of the foregoing.

7. The aqueous composition of claim 6, wherein the quaternary ammonium compound is a ($C_{12}$–$C_{18}$ alkyl) dimethylbenzyl ammonium chloride.

8. The aqueous composition of claim 6, wherein the dialkyldimethylammonium chloride is selected from the group consisting of dioctyldimethylammonium chloride, octyldecyldimethylammonium chloride, didecyldimethylammonium chloride, decylisononyldimethylammonium chloride, diisodecyldimethylammonium chloride, and any combination of any of the foregoing.

* * * * *